United States Patent
Hunt

(10) Patent No.: US 11,724,020 B2
(45) Date of Patent: *Aug. 15, 2023

(54) COLLAPSIBLE SHEET FOR WOUND CLOSURE AND METHOD OF USE

(71) Applicant: Smith & Nephew PLC, Watford (GB)

(72) Inventor: Allan Kenneth Frazer Grugeon Hunt, East Riding (GB)

(73) Assignee: Smith & Nephew PLC, Watford (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/622,773

(22) PCT Filed: Jun. 11, 2018

(86) PCT No.: PCT/EP2018/065400
§ 371 (c)(1),
(2) Date: Dec. 13, 2019

(87) PCT Pub. No.: WO2018/229012
PCT Pub. Date: Dec. 20, 2018

(65) Prior Publication Data
US 2021/0146021 A1 May 20, 2021

Related U.S. Application Data

(60) Provisional application No. 62/519,775, filed on Jun. 14, 2017.

(51) Int. Cl.
*A61M 1/00* (2006.01)
*A61B 46/20* (2016.01)
(Continued)

(52) U.S. Cl.
CPC ............... *A61M 1/90* (2021.05); *A61B 46/20* (2016.02); *A61F 13/00068* (2013.01); *A61F 13/0209* (2013.01); *A61F 2013/00357* (2013.01)

(58) Field of Classification Search
CPC ...... A61M 1/90; A61B 46/20; A61B 17/1325; A61B 17/1322; A61B 17/1327;
(Continued)

(56) References Cited

U.S. PATENT DOCUMENTS 2,245,909 A * 6/1941 Enfiajian ............. A61F 5/05816
128/DIG. 20
3,194,239 A 7/1965 Sullivan et al.
(Continued)

FOREIGN PATENT DOCUMENTS

AU 2012261793 A1 * 1/2013 ............. A61B 17/08
AU 2012261793 B2 11/2014
(Continued)

OTHER PUBLICATIONS

Negative Pressure Wound Therapy Guidelines Copyright 2013 by Smith & Nephew, Inc.*
(Continued)

*Primary Examiner* — Erich G Herbermann
*Assistant Examiner* — Seth Han
(74) *Attorney, Agent, or Firm* — Knobbe, Martens, Olson & Bear LLP

(57) ABSTRACT

Embodiments of a negative pressure wound closure system and methods for using such a system are described. Certain disclosed embodiments facilitate closure of a wound by preferentially exerting a negative pressure on tissue. Some embodiments may utilize a collapsible sheet with a plurality of cells.

20 Claims, 9 Drawing Sheets

(51) Int. Cl.
*A61F 13/00* (2006.01)
*A61F 13/02* (2006.01)

(58) Field of Classification Search
CPC .............. A61B 17/132; A61B 17/135; A61F 13/00068; A61F 13/0209; A61F 13/0226; A61F 13/0216; A61F 5/05808; A61F 5/05816; A61F 5/058; A61F 5/05825; A61F 5/05833; A61F 5/05841; A61F 5/0585; A61F 5/05858; A61F 5/05866; A61F 5/05875; A61F 5/05883; A61F 5/05891; A61F 5/34; A61F 5/32; A61F 5/30; A61F 5/012; A61F 5/0118; Y10S 128/20

See application file for complete search history.

(56) References Cited

U.S. PATENT DOCUMENTS

| | | | |
|---|---|---|---|
| 3,789,851 A | 2/1974 | Leveen |
| 4,467,805 A | 8/1984 | Fukuda |
| 4,608,041 A | 8/1986 | Nielsen et al. |
| 4,699,134 A | 10/1987 | Samuelsen |
| 4,815,468 A | 3/1989 | Annand |
| 5,176,663 A | 1/1993 | Svedman et al. |
| 5,264,218 A | 11/1993 | Rogozinski |
| 5,376,067 A | 12/1994 | Daneshvar |
| 5,409,472 A | 4/1995 | Rawlings et al. |
| 5,415,715 A | 5/1995 | Delage et al. |
| 5,423,857 A | 6/1995 | Rosenman et al. |
| 5,512,041 A | 4/1996 | Bogart |
| 5,562,107 A | 10/1996 | Lavender et al. |
| 5,584,859 A | 12/1996 | Brotz |
| 5,636,643 A | 6/1997 | Argenta et al. |
| 5,695,777 A | 12/1997 | Donovan et al. |
| 6,176,868 B1 | 1/2001 | Detour |
| 6,503,208 B1 | 1/2003 | Skovlund |
| 6,548,727 B1 | 4/2003 | Swenson |
| 6,566,575 B1 | 5/2003 | Stickels et al. |
| 6,685,681 B2 | 2/2004 | Lockwood et al. |
| 6,770,794 B2 | 8/2004 | Fleischmann |
| 6,787,682 B2 | 9/2004 | Gilman et al. |
| 6,977,323 B1 | 12/2005 | Swenson et al. |
| 7,004,915 B2 | 2/2006 | Boynton et al. |
| 7,144,390 B1 | 12/2006 | Hannigan et al. |
| 7,315,183 B2 | 1/2008 | Hinterscher |
| 7,351,250 B2 | 4/2008 | Zamierowski et al. |
| 7,361,184 B2 | 4/2008 | Joshi et al. |
| 7,438,705 B2 | 10/2008 | Karpowicz et al. |
| 7,494,482 B2 | 2/2009 | Orgill et al. |
| 7,615,036 B2 | 11/2009 | Joshi et al. |
| 7,622,629 B2 | 11/2009 | Aali et al. |
| 7,625,362 B2 | 12/2009 | Boehringer et al. |
| 7,683,667 B2 | 3/2010 | Kim et al. |
| 7,700,819 B2 | 4/2010 | Ambrosio et al. |
| 7,754,937 B2 | 7/2010 | Boehringer et al. |
| 7,779,625 B2 | 8/2010 | Joshi et al. |
| 7,815,616 B2 | 10/2010 | Boehringer et al. |
| 7,857,806 B2 | 12/2010 | Karpowicz et al. |
| 7,863,495 B2 | 1/2011 | Aali |
| 7,892,181 B2 | 2/2011 | Christensen et al. |
| 7,896,856 B2 | 3/2011 | Petrosenko et al. |
| 7,909,805 B2 | 3/2011 | Weston et al. |
| 7,910,789 B2 | 3/2011 | Sinyagin |
| 7,931,774 B2 | 4/2011 | Hall et al. |
| 7,942,866 B2 | 5/2011 | Radl et al. |
| 7,951,124 B2 | 5/2011 | Boehringer et al. |
| 7,964,766 B2 | 6/2011 | Blott et al. |
| 7,976,519 B2 | 7/2011 | Bubb et al. |
| 7,976,524 B2 | 7/2011 | Kudo et al. |
| 8,030,534 B2 | 10/2011 | Radl et al. |
| 8,057,447 B2 | 11/2011 | Olson et al. |
| 8,062,331 B2 | 11/2011 | Zamierowski et al. |
| 8,067,662 B2 | 11/2011 | Aali et al. |
| 8,070,773 B2 | 12/2011 | Zamierowski et al. |
| 8,114,126 B2 | 2/2012 | Heaton et al. |
| 8,123,781 B2 | 2/2012 | Zamierowski et al. |
| 8,142,419 B2 | 3/2012 | Heaton et al. |
| 8,172,816 B2 | 5/2012 | Kazala, Jr. et al. |
| 8,187,237 B2 | 5/2012 | Seegert et al. |
| 8,188,331 B2 | 5/2012 | Barta et al. |
| 8,197,467 B2 | 6/2012 | Heaton et al. |
| 8,207,392 B2 | 6/2012 | Haggstrom et al. |
| 8,235,955 B2 | 8/2012 | Blott et al. |
| 8,246,590 B2 | 8/2012 | Hu et al. |
| 8,257,328 B2 | 9/2012 | Augustine et al. |
| 8,273,105 B2 | 9/2012 | Cohen et al. |
| 8,328,776 B2 | 12/2012 | Kelch et al. |
| 8,337,411 B2 | 12/2012 | Nishtala et al. |
| 8,353,931 B2 | 1/2013 | Stopek et al. |
| 8,357,131 B2 | 1/2013 | Olson |
| 8,376,972 B2 | 2/2013 | Fleischmann et al. |
| 8,430,867 B2 | 4/2013 | Robinson et al. |
| 8,447,375 B2 | 5/2013 | Shuler |
| 8,454,990 B2 | 6/2013 | Canada et al. |
| 8,460,257 B2 | 6/2013 | Locke et al. |
| 8,481,804 B2 | 7/2013 | Timothy |
| 8,486,032 B2 | 7/2013 | Seegert et al. |
| 8,500,776 B2 | 8/2013 | Ebner |
| 8,608,776 B2 | 12/2013 | Coward et al. |
| 8,632,523 B2 | 1/2014 | Eriksson et al. |
| 8,673,992 B2 | 3/2014 | Eckstein et al. |
| 8,679,080 B2 | 3/2014 | Kazala, Jr. et al. |
| 8,679,153 B2 | 3/2014 | Dennis |
| 8,680,360 B2 | 3/2014 | Greener et al. |
| 8,708,984 B2 | 4/2014 | Robinson et al. |
| 8,721,629 B2 | 5/2014 | Hardman et al. |
| 8,746,662 B2 | 6/2014 | Poppe |
| 8,764,732 B2 | 7/2014 | Hartwell et al. |
| 8,791,315 B2 | 7/2014 | Lattimore et al. |
| 8,791,316 B2 | 7/2014 | Greener et al. |
| 8,802,916 B2 | 8/2014 | Griffey et al. |
| 8,821,535 B2 | 9/2014 | Greener |
| 8,945,030 B2 | 2/2015 | Weston et al. |
| 9,044,579 B2 | 6/2015 | Blott et al. |
| 9,061,095 B2 | 6/2015 | Adie et al. |
| 9,180,231 B2 | 11/2015 | Greener et al. |
| 9,408,755 B2 | 8/2016 | Larsson et al. |
| 9,421,132 B2 | 8/2016 | Dunn et al. |
| 9,655,807 B2 | 5/2017 | Locke et al. |
| 9,849,023 B2 | 12/2017 | Hall et al. |
| 10,143,485 B2 | 12/2018 | Locke et al. |
| 2001/0034499 A1 | 10/2001 | Sessions et al. |
| 2002/0077661 A1 | 6/2002 | Saadat |
| 2002/0161346 A1 | 10/2002 | Lockwood et al. |
| 2004/0162512 A1 | 8/2004 | Liedtke et al. |
| 2004/0267312 A1 | 12/2004 | Kanner et al. |
| 2005/0142331 A1 | 6/2005 | Anderson et al. |
| 2005/0267424 A1 | 12/2005 | Eriksson et al. |
| 2006/0020269 A1 | 1/2006 | Cheng |
| 2006/0058842 A1 | 3/2006 | Wilke et al. |
| 2006/0069357 A1 | 3/2006 | Marasco |
| 2006/0155260 A1 | 7/2006 | Blott et al. |
| 2006/0217795 A1 | 9/2006 | Besselink et al. |
| 2006/0271018 A1 | 11/2006 | Korf |
| 2007/0052144 A1 | 3/2007 | Knirck et al. |
| 2007/0104941 A1 | 5/2007 | Kameda et al. |
| 2007/0118096 A1 | 5/2007 | Smith et al. |
| 2007/0123973 A1 | 5/2007 | Roth et al. |
| 2007/0129660 A1 | 6/2007 | McLeod et al. |
| 2007/0149910 A1 | 6/2007 | Zocher |
| 2007/0185463 A1 | 8/2007 | Mulligan |
| 2007/0213597 A1 | 9/2007 | Wooster |
| 2007/0282309 A1 | 12/2007 | Bengtson et al. |
| 2008/0041401 A1 | 2/2008 | Casola et al. |
| 2008/0108977 A1 | 5/2008 | Heaton et al. |
| 2008/0243096 A1 | 10/2008 | Svedman |
| 2008/0275409 A1 | 11/2008 | Kane et al. |
| 2008/0306456 A1 | 12/2008 | Riesinger |
| 2009/0005716 A1 | 1/2009 | Abuzaina et al. |
| 2009/0099519 A1 | 4/2009 | Kaplan |
| 2009/0105670 A1 | 4/2009 | Bentley et al. |
| 2009/0204423 A1 | 8/2009 | Degheest et al. |
| 2009/0312685 A1 | 12/2009 | Olsen et al. |

(56) References Cited

U.S. PATENT DOCUMENTS

| | | |
|---|---|---|
| 2010/0022990 A1 | 1/2010 | Karpowicz et al. |
| 2010/0047324 A1 | 2/2010 | Fritz et al. |
| 2010/0081983 A1 | 4/2010 | Zocher et al. |
| 2010/0137775 A1 | 6/2010 | Hu et al. |
| 2010/0150991 A1 | 6/2010 | Bernstein |
| 2010/0160874 A1 | 6/2010 | Robinson et al. |
| 2010/0179515 A1 | 7/2010 | Swain et al. |
| 2010/0198128 A1 | 8/2010 | Turnlund et al. |
| 2010/0262106 A1 | 10/2010 | Hartwell |
| 2010/0280468 A1 | 11/2010 | Haggstrom et al. |
| 2010/0312159 A1 | 12/2010 | Aali et al. |
| 2011/0021965 A1 | 1/2011 | Karp et al. |
| 2011/0022082 A1 | 1/2011 | Burke et al. |
| 2011/0059291 A1 | 3/2011 | Boyce et al. |
| 2011/0066096 A1 | 3/2011 | Svedman |
| 2011/0082480 A1 | 4/2011 | Viola |
| 2011/0110996 A1 | 5/2011 | Schoenberger et al. |
| 2011/0112458 A1 | 5/2011 | Holm et al. |
| 2011/0178451 A1 | 7/2011 | Robinson et al. |
| 2011/0224631 A1 | 9/2011 | Simmons et al. |
| 2011/0224632 A1 | 9/2011 | Zimnitsky et al. |
| 2011/0224634 A1 | 9/2011 | Locke et al. |
| 2011/0264138 A1 | 10/2011 | Avelar et al. |
| 2011/0270301 A1 | 11/2011 | Cornet et al. |
| 2011/0305736 A1 | 12/2011 | Wieland et al. |
| 2012/0016321 A1 | 1/2012 | Wu et al. |
| 2012/0029455 A1 | 2/2012 | Perez-Foullerat et al. |
| 2012/0059412 A1 | 3/2012 | Fleischmann |
| 2012/0130327 A1 | 5/2012 | Marquez |
| 2012/0136326 A1 | 5/2012 | Croizat et al. |
| 2012/0136328 A1 | 5/2012 | Johannison et al. |
| 2012/0143113 A1 | 6/2012 | Robinson et al. |
| 2012/0172926 A1 | 7/2012 | Hotter |
| 2012/0191132 A1 | 7/2012 | Sargeant |
| 2012/0209226 A1 | 8/2012 | Simmons et al. |
| 2012/0209227 A1 | 8/2012 | Dunn et al. |
| 2012/0253302 A1 | 10/2012 | Corley |
| 2012/0302979 A1* | 11/2012 | Locke ............ A61M 1/85 604/319 |
| 2013/0023842 A1 | 1/2013 | Song |
| 2013/0150813 A1 | 6/2013 | Gordon et al. |
| 2013/0190705 A1 | 7/2013 | Vess et al. |
| 2013/0197457 A1 | 8/2013 | Kazala, Jr. et al. |
| 2013/0204213 A1 | 8/2013 | Heagle et al. |
| 2013/0245527 A1 | 9/2013 | Croizat et al. |
| 2013/0325142 A1 | 12/2013 | Hunter et al. |
| 2013/0331757 A1 | 12/2013 | Belson |
| 2014/0094730 A1 | 4/2014 | Greener et al. |
| 2014/0163415 A1 | 6/2014 | Zaiken et al. |
| 2014/0249495 A1 | 9/2014 | Mumby et al. |
| 2014/0296805 A1* | 10/2014 | Arthur ............ A61M 1/784 604/319 |
| 2015/0065968 A1 | 3/2015 | Sealy et al. |
| 2015/0119837 A1 | 4/2015 | Thompson, Jr. et al. |
| 2015/0157758 A1 | 6/2015 | Blücher et al. |
| 2015/0190288 A1 | 7/2015 | Dunn et al. |
| 2015/0196431 A1 | 7/2015 | Dunn et al. |
| 2015/0216732 A1 | 8/2015 | Hartwell et al. |
| 2015/0320602 A1 | 11/2015 | Locke et al. |
| 2015/0374561 A1 | 12/2015 | Hubbard, Jr. et al. |
| 2016/0144085 A1* | 5/2016 | Melin ............ A61M 1/90 604/319 |
| 2016/0184496 A1 | 6/2016 | Jaecklein et al. |
| 2017/0065751 A1 | 3/2017 | Toth et al. |
| 2017/0281838 A1 | 10/2017 | Dunn |
| 2020/0139025 A1* | 5/2020 | Robinson ............ A61M 1/85 |
| 2020/0188564 A1 | 6/2020 | Dunn |
| 2021/0146022 A1 | 5/2021 | Hunt |

FOREIGN PATENT DOCUMENTS

| | | | |
|---|---|---|---|
| AU | 2013206230 B2 | 5/2016 | |
| CN | 101112326 A | 1/2008 | |
| CN | 101744688 A | 6/2010 | |
| CN | 201519362 U | 7/2010 | |
| CN | 102038575 A | 5/2011 | |
| CN | 202568632 U | 12/2012 | |
| CN | 103071197 A | 5/2013 | |
| CN | 203408163 U | 1/2014 | |
| DE | 2949920 A1 | 3/1981 | |
| EP | 1320342 A1 | 6/2003 | |
| EP | 2279016 A1 | 2/2011 | |
| EP | 2567717 A1 | 3/2013 | |
| GB | 2389794 A | 12/2003 | |
| GB | 2423019 A | 8/2006 | |
| GB | 2489947 A | 10/2012 | |
| GB | 2496310 A | 5/2013 | |
| JP | S62-57560 A | 3/1987 | |
| JP | 2012-105840 A | 6/2012 | |
| RU | 1818103 A1 | 5/1993 | |
| RU | 62504 U1 | 4/2007 | |
| WO | WO 01/85248 A1 | 11/2001 | |
| WO | WO 01/89392 A2 | 11/2001 | |
| WO | WO 02/05737 A1 | 1/2002 | |
| WO | WO 03/003948 A1 | 1/2003 | |
| WO | WO 03/049598 A2 | 6/2003 | |
| WO | WO 2005/046761 A1 | 5/2005 | |
| WO | WO 2005/105174 A1 | 11/2005 | |
| WO | WO 2006/046060 A2 | 5/2006 | |
| WO | WO 2008/027449 A2 | 3/2008 | |
| WO | WO 2008/064502 A1 | 6/2008 | |
| WO | WO 2008/104609 A1 | 9/2008 | |
| WO | WO 2009/112062 A1 | 9/2009 | |
| WO | WO 2010/033725 A2 | 3/2010 | |
| WO | WO 2010/097570 A1 | 9/2010 | |
| WO | WO 2011/023384 A1 | 3/2011 | |
| WO | WO 2012/082716 A2 | 6/2012 | |
| WO | WO 2012/082876 A1 | 6/2012 | |
| WO | WO 2012/136707 A1 | 10/2012 | |
| WO | WO 2012/142473 A1 | 10/2012 | |
| WO | WO 2013/012381 A1 | 1/2013 | |
| WO | WO 2013/043258 A1 | 3/2013 | |
| WO | WO 2013/071243 A2 | 5/2013 | |
| WO | WO 2013/076450 A1 | 5/2013 | |
| WO | WO 2013/079947 A1 | 6/2013 | |
| WO | WO 2013/175309 A1 | 11/2013 | |
| WO | WO 2013/175310 A2 | 11/2013 | |
| WO | WO 2014/013348 A2 | 1/2014 | |
| WO | WO 2014/014842 A1 | 1/2014 | |
| WO | WO-2014014871 A1 * | 1/2014 | ........ A61F 13/00068 |
| WO | WO 2014/140578 A1 | 9/2014 | |
| WO | WO 2014/158526 A1 | 10/2014 | |
| WO | WO 2014/165275 A1 | 10/2014 | |
| WO | WO 2014/178945 A1 | 11/2014 | |
| WO | WO 2014/194786 A1 | 12/2014 | |
| WO | WO 2015/008054 A1 | 1/2015 | |
| WO | WO 2015/061352 A2 | 4/2015 | |
| WO | WO-2015061352 A2 * | 4/2015 | ........ A61F 13/00068 |
| WO | WO 2015/109359 A1 | 7/2015 | |
| WO | WO 2015/110409 A1 | 7/2015 | |
| WO | WO 2015/110410 A1 | 7/2015 | |
| WO | WO 2015/169637 A1 | 11/2015 | |
| WO | WO 2015/193257 A1 | 12/2015 | |
| WO | WO 2016/018448 A1 | 2/2016 | |
| WO | WO 2016/176513 A1 | 11/2016 | |
| WO | WO 2016/179245 A1 | 11/2016 | |
| WO | WO 2017/106576 A1 | 6/2017 | |
| WO | WO 2018/038665 A1 | 3/2018 | |
| WO | WO 2018/041805 A1 | 3/2018 | |
| WO | WO 2018/044944 A1 | 3/2018 | |
| WO | WO 2018/044949 A1 | 3/2018 | |
| WO | WO 2018/085457 A1 | 5/2018 | |
| WO | WO 2018/140386 A2 | 8/2018 | |
| WO | WO 2018/237206 A2 | 12/2018 | |

OTHER PUBLICATIONS

"Definition of 3D Printer," American Heritage Dictionary of the English Language, Fifth Edition, accessed on Feb. 22, 2018 from URL: https://www.thefreedictionary.co, 2016, 1 page.

"Definition of Adhere," The Free Dictionary, accessed on Mar. 23, 2017 from http://www.thefreedictionary.com/adhere, 6 pages.

(56) References Cited

OTHER PUBLICATIONS

"Definition of Oculiform," Webster's Revised Unabridged Dictionary, accessed from The Free Dictionary on May 30, 2018 from URL: https://www.thefreedictionary.com/Oculiform, 1913, 1 page.

"Definition of Throughout," Merriam-Webster Dictionary, accessed on Aug. 29, 2017 from https://www.merriam-webster.com/dictionary/throughout, 11 pages.

Hougaard, et al., "The Open Abdomen: Temporary Closure with a Modified Negative Pressure Therapy Technique," International Wound Journal, ISSN 1742-4801, 2014, pp. 13-16.

Kapischke M., et al., "Self-Fixating Mesh for the Lichtenstein Procedure-a Prestudy," Langenbecks Arch Surg, 2010, vol. 395, pp. 317-322.

International Search Report and Written Opinion for Application No. PCT/EP2018/065400, dated Sep. 27, 2018, 12 pages.

International Preliminary Report on Patentability for Application No. PCT/EP2018/065400, dated Dec. 26, 2019, 10 pages.

Jin S.G., et al., "Influence of Hydrophilic Polymers on Functional Properties and Wound Healing Efficacy of Hydrocolloid Based Wound Dressings," Int J Pharm, Mar. 30, 2016, vol. 501 (1-2), pp. 160-166.

\* cited by examiner

COLLAPSIBLE SHEET FOR WOUND CLOSURE AND METHOD OF USE

CROSS-REFERENCE TO RELATED APPLICATIONS

This application is a U.S. national stage application of International Patent Application No. PCT/EP2018/065400, filed Jun. 11, 2018, which claims priority to U.S. Provisional Application No. 62/519,775 filed on Jun. 14, 2017, which is incorporated by reference in its entirety.

BACKGROUND

Field of Use

This application describes embodiments of apparatuses, methods, and systems for the treatment of wounds, specifically to aid in the closure of large wounds.

Description of the Related Art

Acute compartment syndrome occurs when tissue pressure within a closed muscle compartment exceeds the perfusion pressure and it most commonly occurs in compartments in the leg or arm. Fasciotomy is a surgical procedure to treat acute compartment syndrome. Fasciotomy consists of one or more fascial incisions to permit decompression of the compartments, and as such, a large wound may be created onto the patient. Closure of this wound, while minimizing the risk of secondary infections and other complications, and after the underlying edema has subsided, then becomes a priority. Other large or incisional wounds, either as a result of surgery, trauma, or other conditions, may also require closure. Wound dehiscence of existing wounds is another complication that may arise, possibly due to incomplete underlying fascial closure, or secondary factors such as infection.

The treatment of open or chronic wounds by means of applying negative pressure to the site of the wound, where the wounds are too large to spontaneously close or otherwise fail to heal is well known in the art. Negative pressure, in many cases, can improve the rate of healing while also removing exudates and other deleterious substances from the wound. Negative pressure wound treatment systems currently known in the art commonly involve placing a cover that is impermeable to liquids over the wound, using various mechanisms to seal the cover to the tissue of the patient surrounding the wound, and connecting a source of negative pressure (such as a vacuum pump) to the cover whereby an area of negative pressure is created under the cover in the area of the wound.

However, existing negative pressure treatment systems, while permitting eventual wound closure, still require lengthy closure times. Although these may be combined with other tissue securement means, such as sutures, there is also a risk that underlying muscular and fascial tissue is not appropriately reapproximated so as to permit complete wound closure. Further, when foam or other wound fillers are inserted into the wound, the application of negative pressure to the wound and the foam may cause atmospheric pressure to bear down onto the wound, compressing the foam downward and outward against the margins of the wound. This downward compression of the wound filler slows the healing process and slows or prevents the joining of wound margins. Additionally, inflammation of the fascia in the form of certain types of fasciitis can lead to rapid and excessive tissue loss, potentially meriting the need for more advanced negative pressure treatment systems. Accordingly, there is a need to provide for an improved apparatus, method, and system for the treatment and closure of wounds.

SUMMARY

Certain disclosed embodiments relate to negative pressure wound closure devices, methods, and systems that facilitate closure of a wound. It will be understood by one of skill in the art that the wounds described may encompass any wound, and are not limited to a particular location or type of wound. Further, it will be understood by one of skill of art that application of the devices, methods, and systems described herein are not limited to the closure of wound or any other particular use. The devices, methods, and systems may operate to reduce the need for repetitive replacement of wound filler material currently employed and can advance the rate of healing. The devices, methods, and systems may be simultaneously used with negative pressure to remove wound fluids.

In some embodiments, a wound closure device may comprise a collapsible sheet configured to be placed over a wound. The collapsible sheet comprises:
  a top layer and a bottom layer; and
  a plurality of cells at least partially defined by the top layer and the bottom layer, the plurality of cells arranged side-by-side;
  wherein each cell has a tessellating shape, and
  wherein at least one of the plurality of cells is configured to collapse in a vertical plane of the collapsible structure and thereby cause the collapsible sheet to collapse.

In some embodiments, at least some of the cells may be inflatable. At least one of the top layer or the bottom layer may comprise flexible thin film material. At least some of the cells may be configured to collapse when negative pressure is applied to the collapsible sheet.

In some embodiments, at least one cell may have a hexagonal shape. The plurality of cells may have uniform size and shape, or at least some of the plurality of cells may have non-uniform size and/or shape. In some embodiments, the collapsible sheet may further comprise a cell wall. The cell wall may be inflatable. The collapsible sheet further comprises an indicator on one or more cells configured to indicate a direction where the collapsible sheet will collapse upon collapse of any particular cell.

In some embodiments, the collapsible sheet may be configured to cover the wound and form a seal around the wound. The wound closure device may further comprise a suction port configured to supply negative pressure to the wound and/or a tissue protection layer configured to be positioned over the wound below the collapsible sheet. The port may be integrated in the collapsible sheet. The port may comprise a valve including superabsorbent material configured to swell and at least partially close the valve when a rate of absorption of wound fluid is greater than a rate of evaporation of wound fluid. The bottom surface of the collapsible sheet may comprise one or more gaps between cells. The wound closure device may further comprise one or more drapes configured to cover the collapsible sheet and form a seal around the wound.

In certain embodiments, a method of treating a wound comprises placing the collapsible sheet over the wound. The method may further comprise applying or causing application of negative pressure through the collapsible sheet to the wound, wherein the application of negative pressure causes the collapsible sheet to collapse. The method may further comprise placing a tissue protection layer over the wound before placing the collapsible sheet.

Other embodiments of an apparatus for use with negative pressure, devices and associated methods are described below.

DETAILED DESCRIPTION

Figure 1:
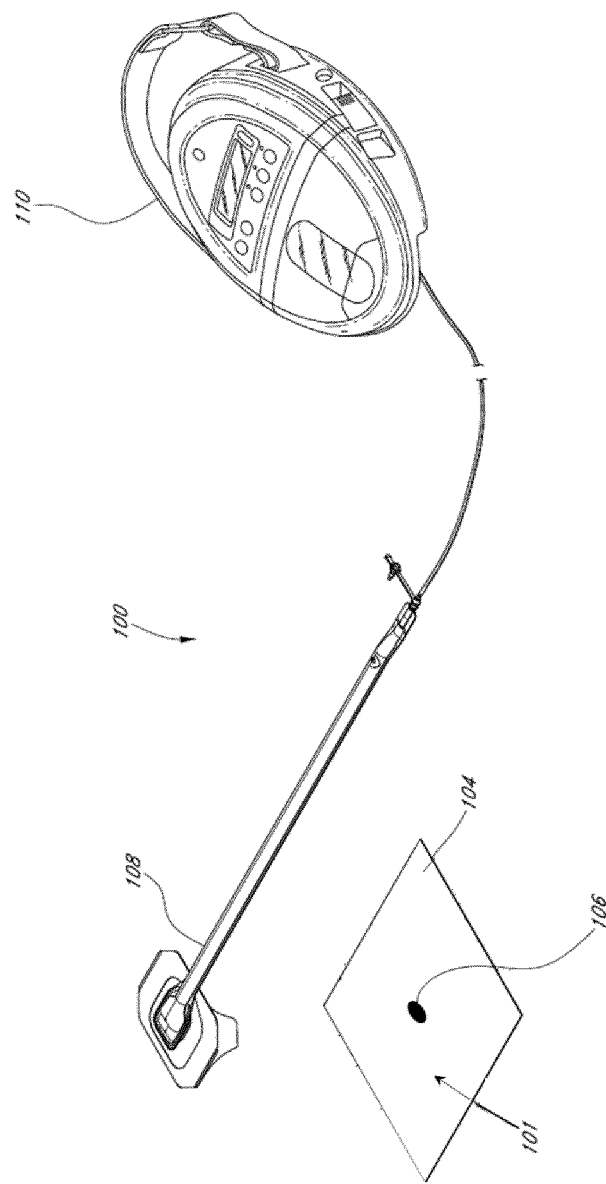
FIG. 1 illustrates an embodiment of a negative pressure treatment system.

Embodiments disclosed in this section or elsewhere in this specification relate to apparatuses and methods of treating a wound with reduced pressure, including pump and wound dressing components and apparatuses. The apparatuses and components comprising the wound overlay and packing materials, if any, are sometimes collectively referred to in this section or elsewhere in this specification as dressings.

It will be appreciated that throughout this specification reference is made to a wound. It is to be understood that the term wound is to be broadly construed and encompasses open and closed wounds in which skin is torn, cut or punctured or where trauma causes a contusion, or any other superficial or other conditions or imperfections on the skin of a patient or otherwise that, in some cases, benefit from reduced pressure treatment. A wound is thus broadly defined as any damaged region of tissue where fluid may or may not be produced. Examples of such wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, amputation wounds, flaps and skin grafts, lacerations, abrasions, contusions, burns, electrical burns, diabetic ulcers, pressure ulcers, stoma, surgical wounds, trauma and venous ulcers or the like.

As is used in this section or elsewhere in this specification, reduced or negative pressure levels, such as –X mmHg, represent pressure levels that are below standard atmospheric pressure, which typically corresponds to 760 mmHg (or 1 atm, 29.93 inHg, 101.325 kPa, 14.696 psi, etc.). Accordingly, a negative pressure value of –X mmHg reflects absolute pressure that is X mmHg below, for example, 760 mmHg or, in other words, an absolute pressure of (760–X) mmHg. In addition, negative pressure that is "less" or "smaller" than –X mmHg corresponds to pressure that is closer to atmospheric pressure (e.g., –40 mmHg is less than –60 mmHg). Negative pressure that is "more" or "greater" than –X mmHg corresponds to pressure that is further from atmospheric pressure (e.g., –80 mmHg is more than –60 mmHg).

The negative pressure range for some embodiments of the present disclosure can be approximately –80 mmHg, or between about –10 mmHg and –200 mmHg. Note that these pressures are relative to normal ambient atmospheric pressure. Thus, –200 mmHg would be about 560 mmHg in practical terms. In some embodiments, the pressure range can be between about –40 mmHg and –150 mmHg. Alternatively, a pressure range of up to –75 mmHg, up to –80 mmHg or over –80 mmHg can be used. Also in other embodiments a pressure range of below –75 mmHg can be used. Alternatively, a pressure range of over approximately –100 mmHg, or even –150 mmHg, can be supplied by the negative pressure apparatus. In some embodiments, the negative pressure range can be as small as about –20 mmHg or about –25 mmHg, which may be useful to reduce fistulas. In some embodiments of wound closure devices described here, increased wound contraction can lead to increased tissue expansion in the surrounding wound tissue. This effect may be increased by varying the force applied to the tissue, for example by varying the negative pressure applied to the wound over time, possibly in conjunction with increased tensile forces applied to the wound via embodiments of the wound closure devices. In some embodiments, negative pressure may be varied over time for example using a sinusoidal wave, square wave, and/or in synchronization with one or more patient physiological indices (e.g., heartbeat).

Examples of such applications where additional disclosure relating to the preceding descriptions may be found include U.S. Pat. No. 8,235,955, titled "Wound treatment apparatus and method," issued Aug. 7, 2012 and U.S. Pat. No. 7,753,894, titled "Wound cleansing apparatus with stress," issued Jul. 13, 2010. Both applications are hereby incorporated by reference in their entirety. Other applications that may contain teachings relevant for use with the embodiments described in this section or elsewhere in this specification may include application Ser. No. 12/886,088, titled "Systems And Methods For Using Negative Pressure Wound Therapy To Manage Open Abdominal Wounds," filed Sep. 20, 2010, published as US 2011/0213287; application Ser. No. 13/092,042, titled "Wound Dressing And Method Of Use," filed Apr. 21, 2011, published as US 2011/0282309; and application Ser. No. 13/365,615, titled "Negative Pressure Wound Closure Device," filed Feb. 3, 2012, published as US 2012/0209227, the entireties of each of which are hereby incorporated by reference. Still more applications that may contain teachings relevant for use with the embodiments described in this specification are application Ser. No. 13/942,493, titled "Negative Pressure Wound Closure Device," filed Jul. 15, 2013, published as US 2014/0180225; PCT App. No. PCT/US2013/050619, filed Jul. 16, 2013 titled "Negative Pressure Wound Closure Device," published as WO 2014/014871 A1; PCT App. No. PCT/US2013/050698, filed Jul. 16, 2013 titled "Negative Pressure Wound Closure Device," published as WO 2014/014922 A1; PCT App. No. PCT/IB2013/01555, titled "Devices and Methods for Treating and Closing Wounds with Negative Pressure," filed May 5, 2013, published as WO 2013/175309 A1; PCT App. No. PCT/US2014/025059, titled "Negative Pressure Wound Closure Device and Systems and Methods of Use in Treating Wounds with Negative Pressure," filed Mar. 12, 2014, published as WO 2014/165275 A1; PCT App. No. PCT/GB2014/050746, "Compressible Wound Fillers and Systems and Methods of Use In Treating Wounds With Negative Pressure," filed Mar. 13, 2014, published as WO 2014/140578 A1; PCT App. No. PCT/US2014/061627, titled "Negative Pressure Wound Closure Device," filed Oct. 21, 2014, and published as 2016/0287765 A1; and PCT App. No. PCT/US2016/029888, titled "Negative Pressure Wound Closure Device," filed Apr. 28, 2016, published as WO 2016/176513. Each of the aforementioned applications is hereby incorporated by reference in its entirety and should be considered part of the present specification.

As used in this section or elsewhere in this specification, the term "horizontal," when referring to a wound, indicates a direction or plane generally parallel to the skin surrounding the wound. The term "vertical," when referring to a wound, generally refers to a direction extending perpendicular to the horizontal plane. The term "longitudinal," when referring to a wound, generally refers to a direction in the horizontal plane taken in a direction along which the wound is longest. The term "lateral," when referring to a wound, generally refers to a direction in the horizontal plane perpendicular to the longitudinal direction. The terms "horizontal," "vertical," "longitudinal," and "lateral" may also be used to describe the collapsible sheets and wound closure devices described throughout this specification. When describing these structures or devices, these terms should not be construed to require that the structures or devices necessarily be placed into a wound in a certain orientation, though in certain embodiments, it may be preferable to do so.

FIG. 1 illustrates an embodiment of a negative pressure treatment system 100 that comprises a wound closure device 104 in and/or over a wound 101. The wound closure device 104 may comprise one or more embodiments of collapsible sheets described in further detail in this section or elsewhere in this specification. In some embodiments, a single drape or multiple drapes (not shown here) may be placed over the wound closure device 104, and is preferably adhered or sealed to the skin on the periphery of the wound 101 so as to create a fluid-tight seal. An aperture 106 may be made through the wound closure device 104 or the drape, which can be manually made or preformed into the wound closure device 104 or drape so as to provide a fluidic connection from the wound 101 to a source of negative pressure such as a pump 110. Preferably, the fluidic connection between the aperture 106 and the pump 110 is made via a conduit 108. In some embodiments, the conduit 108 may comprise a RENASYS® Soft Port™, manufactured by Smith & Nephew. Of course, in some embodiments, the wound closure device 104 or the drape may not necessarily comprise an aperture 106, and the fluidic connection to the pump 110 may be made by placing the conduit 108 below the wound closure device 104 or the drape. In some wounds, particularly larger wounds, multiple conduits 108 may be used, fluidically connected via one or more apertures 106.

In use, the wound 101 may be prepared and cleaned. In some cases, a non- or minimally-adherent tissue protection layer (not illustrated) may be applied over any exposed internal tissue. The wound 101 is then covered with wound closure device 104, optionally so as to form a fluid-tight seal. In some embodiments, the wound 101 and the wound closure device 104 further covered with the drape so as to form a fluid-tight seal. A first end of the conduit 108 is then placed in fluid communication with the wound, for example via the aperture 106. The second end of the conduit 108 is connected to the pump 110. The pump 110 may then be activated so as to supply negative pressure to the wound 101 and evacuate wound exudate from the wound 101. As will be described in additional detail herein and in relation to the embodiments of the foregoing wound closure devices, negative pressure may also aid in promoting closure of the wound 101, for example by approximating opposing wound margins.

Any structure or component disclosed in this section or elsewhere in the specification may comprise a radiopaque material. A radiopaque material advantageously allows a clinician to more easily find pieces of the disclosed wound closure device that may have come loose from the structure and become lost in the wound. Some examples of radiopaque materials include barium sulfate, bismuth trioxide, bismuth subcarbonate, bismuth oxychloride, and tungsten.

Collapsible Sheet

Figure 2:
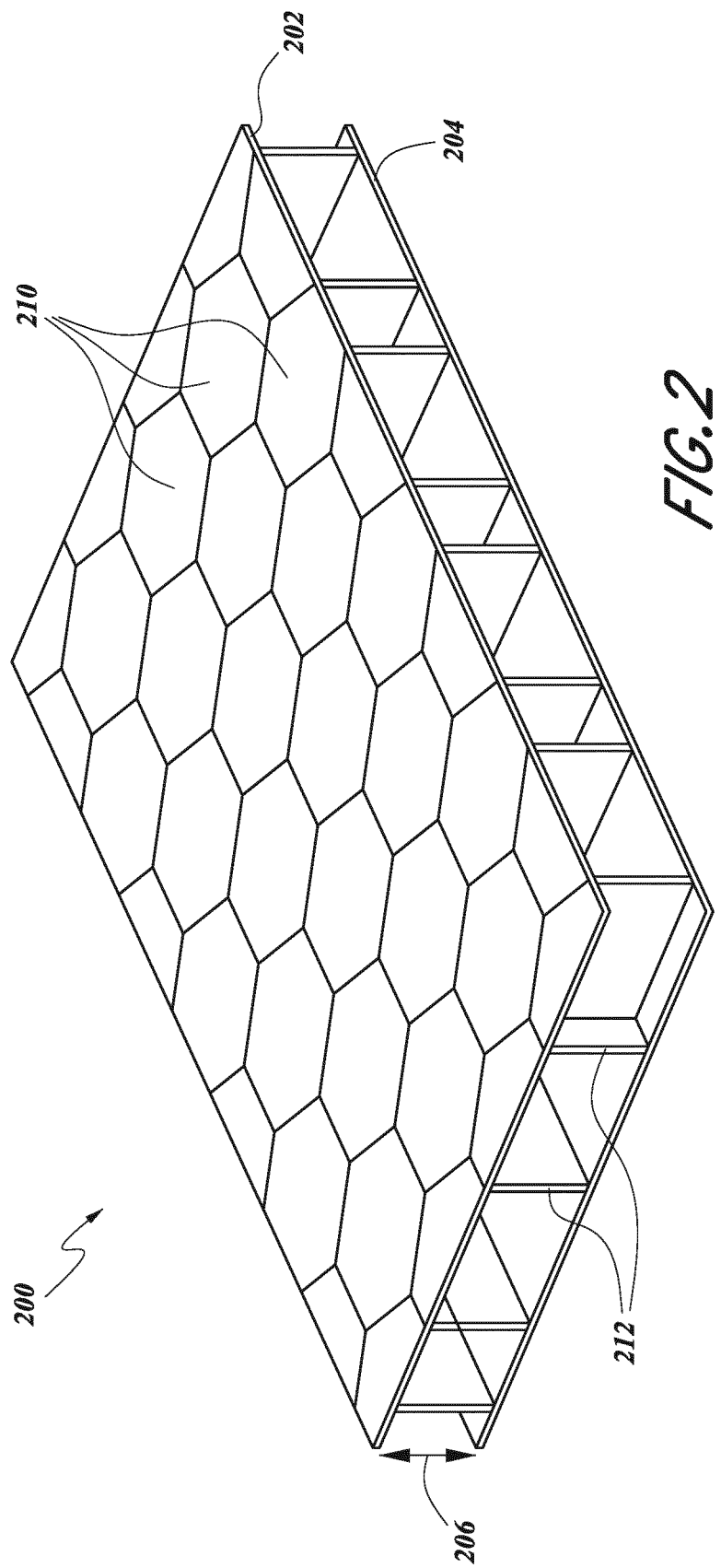
FIG. 2 illustrates an embodiment of a collapsible sheet.

A wound closure device as described in this section or elsewhere in the specification may include a collapsible sheet. FIG. 2 illustrates an embodiment of a collapsible sheet 200. The collapsible sheet 200 may include a top layer 202, a bottom layer 204, and an intermediate volume or space 206 between the top layer 204 and the bottom layer 204. The collapsible sheet 200 may have a plurality of cells 210 which is provided by side-by-side. Cells 210 may be defined by a portion of the top layer 202, a portion of the bottom layer 204, and cell walls 212 extending from the top layer 204 to the bottom layer 204 along the intermediate space 206 between the top layer 204 and the bottom layer 204. In some embodiments, the collapsible sheet 200 may not have cell walls 212, and cells 210 may be formed by welding the top layer 204 and the bottom layer 208 in desired patterns, such that the cells are defined only by top layer 204 and the bottom layer 208. As will be described in greater detail herein, the size and shape of cells 210 may be designed so as to facilitate greater closure of the wound. In some embodiments, the collapsible sheet is tearable, such that the sheet may be shaped into the shape of a wound and/or sized into the size of a wound. As described elsewhere in the specification, tears may be completed at the cell walls 212, or at any other suitable locations.

All collapsible sheets described in this section or elsewhere in the specification may be fashioned to accommodate any size of wound. However, to better accommodate the needs of the clinical environment, in certain embodiments, collapsible sheets described herein may be provided in a pack of two sizes, one smaller collapsible sheet and one larger collapsible sheet about 1.25 times as larger, about 1.5 times as large, about 1.75 times as large, about 2 times as larger, about 2.5 times as larger, about 3 times as large, about 4 times as large, about 5 times as large, or more than about 5 times as large. In some embodiments, the pack may comprise more than two sizes, such as three sizes, four sizes, five sizes, or more than five sizes. The collapsible sheet within the pack may be of a variety of sizes in relation to one another such as the ratios described herein. In some embodiments, a large collapsible sheet may be provided, such that it can be cut into a desirable size, or torn along an optional pre-cut.

Collapsible sheets described in this section or elsewhere in the specification, may be applied on the wound. In some embodiments, a tissue protection layer may be placed or positioned in and/or on the wound, before placement of the collapsible sheet. In some embodiments, the collapsible sheet may be adhered or sealed to the skin on the periphery of the wound so as to create a fluid-tight seal, and the negative pressure may be provided beneath the collapsible sheet. In some embodiments, the drape may be provided above the collapsible sheet and may be adhered or sealed to the skin on the periphery of the wound so as to create a fluid-tight seal, and the negative pressure may be provided beneath the drape and/or the collapsible sheet.

In certain embodiments, the collapsible sheet 200 can collapse in any manner described in this section or elsewhere in this specification with or without the application of negative pressure. For example, the collapsible sheet may collapse significantly more in one plane than in another plane, upon application of negative pressure. In some embodiments, the collapsible sheet may collapse more in a vertical plane parallel to the thickness of the collapsible sheet than in a horizontal plane parallel to the length and width of the collapsible sheet. In some embodiments, particular cells may collapse in a first direction, while another cells may collapse in the same or other direction. The collapsible sheet may be comprised of any materials described in this section or elsewhere in this specification, including one or more of flexible plastics such as silicone, polyurethane, rigid plastics such as polyvinyl chloride, semi-rigid plastics, semi-flexible plastics, biocompatible materials, composite materials, metals, and foam. In certain embodiments, the collapsible sheet may comprise a radio opaque material, to more readily allow a clinician to find pieces of the collapsible sheet within the wound.

Returning to FIG. 2, the collapsible sheet 200 may have an outer perimeter that defines a rectangular shape. In some embodiments, the collapsible sheet 200 may have a circular shape, hexagonal shape, or another suitable shape that substantially matches the shape of a wound. As described herein, the collapsible sheet 200 may comprise a plurality of cells 210 provided side-by-side, each cell defined by one or more walls 212, and each cell 210 having a top end and a bottom end defined by top layer 202 and the bottom layer 204. As with the other collapsible sheets described in this section and elsewhere in the specification, the collapsible sheet 200 may collapse by collapsing one or more cells 210. In some embodiments, the cells 210 are all of the same approximate shape and/or size; however, in other embodiments, at least some of the cells are of different shapes and/or sizes. In some embodiments, the collapsible sheets as described in this section or elsewhere in the specification include one or more cells having tessellating shapes, such as a hexagonal shape. The cells may be arranged in a honeycomb-like pattern. In certain embodiments, cells may have other tessellating shapes, such as triangles, squares, rectangles, polygons, etc. In some embodiments, the sheet may have cells with two or more different types of shapes provided side-by side (e.g., squares and triangles; hexagons and triangles; hexagons, squares and triangles, and the like).

The collapsible sheet 200 may be made from one single material, such as those described elsewhere in the specification, or the collapsible sheet may be made from multiple materials. For example, cell walls 212 may be constructed from more rigid material while the top layer 202 and the bottom layer 204 may be constructed from more flexible material. The top layer 202 and the bottom layer 204 may have flat surface or uneven surface. In some embodiments, the top layer 202 and/or the bottom layer 204 may have embossed surface as cells 210 are bulged out on their top and/or bottom end. In some embodiments, the top layer 202 and/or the bottom layer 204 may be flat in their natural state, but constructed from flexible material such that cells 210 can be bulged out on their top and/or bottom end when cells are inflated.

The collapsible sheet 200 and all collapsible sheets and wound closure devices described in this section or elsewhere in this specification can collapse on a variety of timescales in a dynamic fashion. In certain embodiments, the majority of the collapse may occur within the first few minutes upon application of negative pressure. However, after the initial collapse, the collapsible sheet or wound closure device may continue to collapse at a much slower rate, thereby applying increasing tension over a long period of time and drawing the edges of the wound closer together. By slowly drawing the wound edges closer together over time, the collapsible sheet or wound closure device allows the surrounding healing tissue to remodel synergistically with the closure of the device or collapsible sheet. Slow, dynamic wound closure may allow the surrounding tissue to heal at an accelerated rate, because the collapsing sheet or device slowly brings the edges of the wound closer together without stressing the newly formed or weakened tissue too quickly.

In certain embodiments, up to 90% of the collapse of the collapsible sheet or wound closure device may occur within the first few minutes upon application of negative pressure, while the remaining 10% of the collapse may occur slowly over a period of many minutes, hours, days, weeks, or months. In other embodiments, up to about 80% of the collapse, up to about 70%, up to about 60%, up to about 50%, up to about 40%, up to about 30%, up to about 20%, up to about 10%, or about 0% of the collapse will occur within the first few minutes upon application of negative pressure while the remainder of the collapse occurs at a much slower rate such as over the course of many minutes, hours, days weeks, or months. In other embodiments, the collapsible sheet can collapse at a variable rate. In some embodiments, the entirety of the collapse occurs at a slowed rate, while in other embodiments the entirety of the collapse occurs almost immediately within the first few minutes. In further embodiments, the collapse can occur at any rate and the rate can vary over time. In certain embodiments, the rate of collapse can be altered in a variable fashion by adding and/or removing portions of the structure or by controlling the application of negative pressure and irrigant fluid.

In some embodiments, the collapsible sheet 200 may be inflatable. The collapsible sheet may be constructed from flexible film material, for example polyurethane, such that cells 210 may be filled with fluid, such as air, and inflated. In some embodiments, the collapsible sheet 200 is constructed from a top layer 202, a bottom layer 204, and optional cell walls 220 each constructed from flexible film material, for example polyurethane, and adhered to one another for example by adhesive, heat welding, radio frequency welding, laser welding, or ultrasonic welding. In some embodiments, each of the cells 210 of the collapsible sheet 200 is completely enclosed by the top layer 202, the bottom layer 204, and cell walls 220, such that space within each of the cell 210 is fluidically isolated and inflated to maintain its shape unless the cell is punctured, like bubbles in bubble wraps. In embodiments of inflatable collapsible sheets, the top layer, the bottom layer and cell walls may be constructed from flexible film material which can withstand the fluid pressure within the inflated cell, such that cells do not burst without puncturing or cutting.

In some embodiments, the collapsible sheet 200 may include a valve or port, such that cells can be reversibly inflated. In addition to, or alternatively to the foregoing, collapsible sheets may have a mechanism that permits inflated cells to be sealed without manually closing the valve or port. For example, in some embodiments, a collapsible sheet includes one or more one-way or non-return valves at one or more junctions between the fluid channel (which can be an air channel) and a cell.

In some embodiments, the collapsible sheet 200 can be at least partially constructed from relatively rigid polymer materials, such that the collapsible sheet 200 and cells 210 can withstand greater strength and maintain its structure even without being inflated. While collapsible sheets constructed from more flexible and thinner material can be used for curved regions such as arms or legs, collapsible sheets constructed from more rigid collapsible sheets can be used in wider regions such as sacral regions. The collapsible sheet 200 can be constructed from both relatively flexible film materials and relatively rigid polymer materials. For example, in some embodiments, the top layer 202 and the bottom layer 204 are constructed from flexible film layers such that cells 210 can be inflated, while cell walls are constructed from more rigid materials to help the collapsible sheet 200 to maintain its structure.

Any of the collapsible sheets described in this section or elsewhere in the specification may be constructed using any suitable methods. For example, the collapsible sheets may be constructed via molding or may be printed directly using 3D printing technology. In certain embodiments, the collapsible sheets of FIG. 2 may be constructed from a single polymer via 3D printing. In some embodiments, the collapsible sheets may be constructed from one polymer, two polymers, three polymers, or more than three polymers. The collapsible sheets may be constructed from any material disclosed in this section or elsewhere in the specification. The collapsible sheet can be made by cutting the structure out of a solid block of material. Methods used for cutting can include, for example, water jet cutting, laser cutting, or die cutting. The collapsible sheets may be cut to size along the walls of the cells 200 and/or along any portions of the collapsible sheet.

In some embodiments, the collapsible sheet 200 of FIG. 2 includes perforations or detachable sections that allow portions of the device to separate from the remainder of the device. For example, perforations may be incorporated into cell walls 212 between cells 210 contained within the collapsible sheet 200, allowing for the removal of individual cells to alter the shape of the collapsible sheet 200. Applicable to all collapsible sheets or wound closure devices described in this section or elsewhere in the specification, the collapsible sheet or wound closure device may be tearable such that the collapsible sheet may be shaped into the shape of a wound. In some embodiments, the collapsible sheet may be torn along the cell wall, while in further embodiments, the elongate strips or intervening members may be torn at any suitable position.

In some embodiments, the collapsible sheet 200 can be constructed from a transparent material such that the user of the collapsible sheet or the wound closure device can adjust the collapsible sheet relative to the wound, and monitor the wound or tissue beneath the collapsible sheet 200.

Collapsing of Collapsible Sheet

Figure 3:
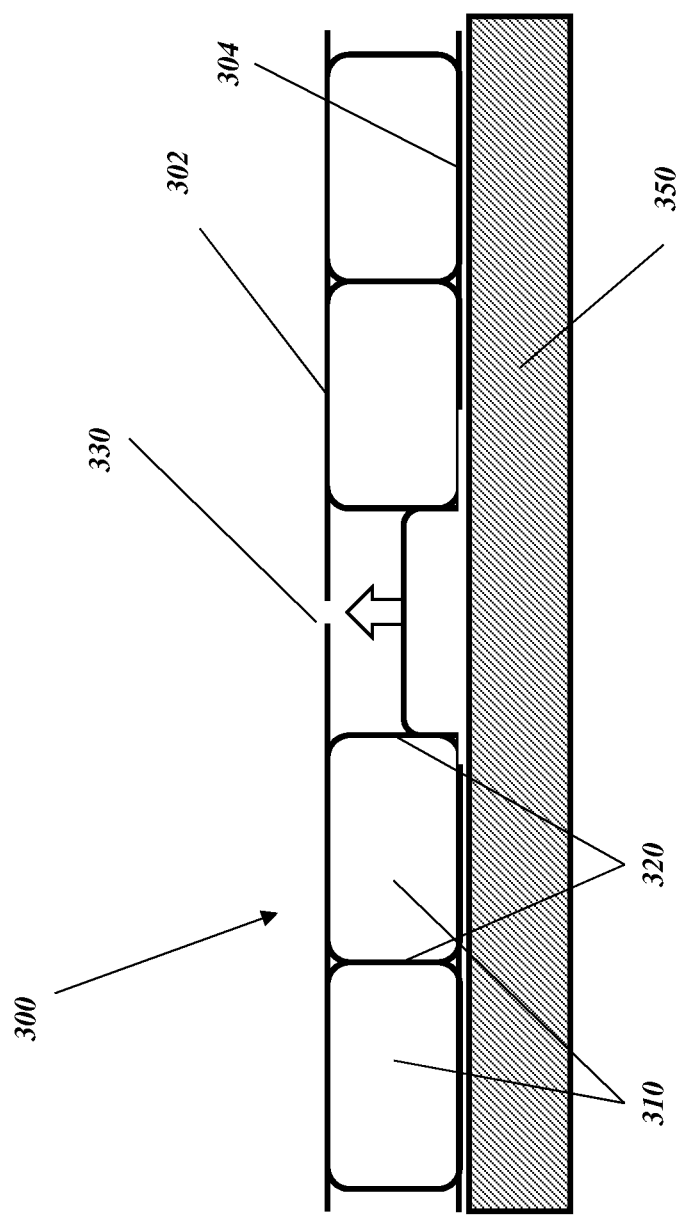
FIG. 3 illustrates collapse of a collapsible sheet according to an embodiment.

FIG. 3 illustrates a cross-sectional view of an embodiment of a collapsible sheet 300 similar to the collapsible sheet 200 of FIG. 2 and placed on a tissue 350. The collapsible sheet 300 includes cells 310 provided side-by-side. The cells 310 can be inflatable and are defined by cell walls 320, a top layer 302 and a bottom layer 304 like cells 210 in FIG. 2. In some embodiments, each of cells 310 has hollow space enclosed by cell walls 320, a portion of the top layer, and a portion of the bottom layer. Each hollow space of cells 310 may be filled with fluid, such as air, and/or the cells 310 may be inflatable.

As described in elsewhere in the specification, the collapsible sheet 300 may collapse by collapsing one or more cells 310. When each of cells 310 is filled with, for example, air and/or each of cells are inflated, none of the cells 310 may collapse. In fact, cells 310 may expand in a negative pressure environment as the air pressure outside the cell would be lower than the pressure inside the cell. However, when one or more inflated cells 310 is deflated, for example by puncturing a hole 330 and exposing the interior volume of the cell to the exterior environment, the cell 310 may collapse with negative pressure as indicated by the arrows in FIG. 3. Upon application of negative pressure around the collapsible sheet, such effect will be greater.

Figure 4:
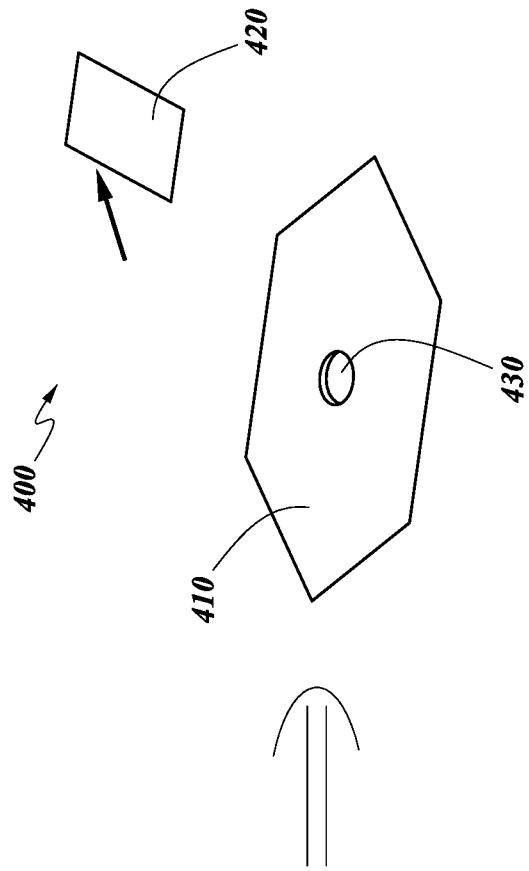
FIG. 4 illustrates a part of a collapsible sheet according to an embodiment.
Figure 4:
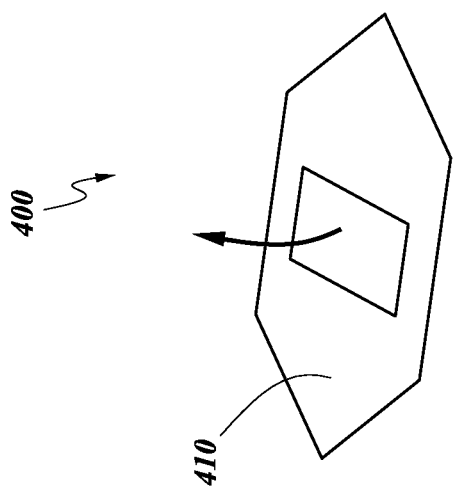

In some embodiments, the cell 310 may be collapsed by puncturing one or more holes 330 on the top layer 302 and/or the bottom layer 304 of the collapsible sheet 300. In some embodiments, cells may have one or more holes which can be reversibly open or closed. For example, as shown in FIG. 4, a cell 410 may include detachable closure, which can be a tab 420, which covers the opening 430 on the top layer and/or the bottom layer when attached and uncovers the opening 430 when detached. In some embodiments, such tab may be only partially detached, such that the end of the tab remains attached to the collapsible sheet and act as a hinge. In some embodiments, the tab may be constructed to be attached and detached repetitively, and cells may be constructed to withstand multiple cycles of inflation and deflation. In some embodiments, cells may include other mechanisms to reversibly collapse, such as valves or any other suitable means.

In some embodiments, one or more cells of collapsible sheets can be deflated by exposing cells to the negative pressure, or directly applying negative pressure to one or more cells, in addition to methods described in this section or elsewhere in the specification, such as puncturing or opening tabs. By directly applying negative pressure, one may deflate a cell of a collapsible sheet regardless of whether the cell is inflatable. For example, a non-inflatable collapsible sheet which is constructed from more rigid polymer material may collapse while such collapsible sheet may not substantially collapse from puncturing. Further, applying negative pressure directly to the cell may also facilitate collapse of the cell of the inflatable collapsible sheets and increase degree of collapse from its deflated state, such that facilitating greater closure of the wound.

Returning to FIG. 3, in some embodiments, punctured/opened cell(s) may collapse by lifting the bottom layer 304 and/or dropping the top layer 302. Cell(s) may be constructed such that cell may collapse only toward certain direction. For example, in some embodiments, a cell may have more rigid top layer and more flexible bottom layer around it, such that the cell may collapse more by lifting the bottom layer. In some embodiments, plurality of cells are constructed to collapse in the same direction. In some embodiments, plurality of cells are constructed to collapse in different directions. In some embodiments, the collapsible sheet may collapse in the horizontal plane of it when multiple adjacent cells are deflated and collapse in the horizontal plane. Collapsible sheets with different collapsing pattern may be provided in one kit, such that a practitioner may choose depending on the shape or size of wound (e.g., linear wound, curved wound, circular wound, etc.).

Figure 8:
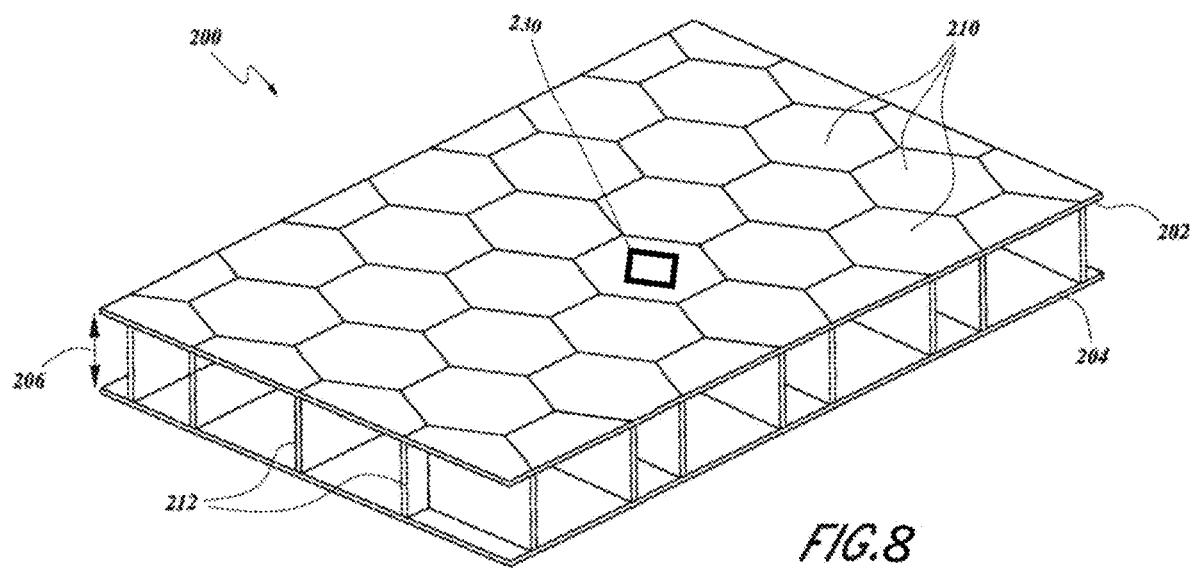
FIG. 8 illustrates a side view of an embodiment of a portion of a fluid transport dressing.

When different cells collapse in different directions, the direction of collapse may be visually indicated on the cell or tab for the convenience of a practitioner. For example, with reference to FIG. 8, a tab 230 similar with the detachable tab 420 of FIG. 4 may have a directional marker on it to indicate the direction that the cell will collapse or the direction of the resulting force applied by the negative pressure when that tab is removed. The directional marker may be arrows, colors or any other suitable means. In some embodiments, the directional marker can be numbers. For example, detaching all tabs with a number 3 on them will cause a linear collapse of the collapsible sheet along the horizontal plane of the collapsible sheet, while detaching all tabs with a number 1 will cause only collapse in vertical direction.

As disclosed elsewhere in the specification, the negative pressure may be provided beneath the collapsible sheet 300. In some embodiments, such as shown in FIG. 3, when one or more cells 310 collapse, it may provide a hollow space beneath it such that the tissue directly beneath the collapsed cell is exposed to the negative pressure provided beneath the collapsible sheet 300. In some embodiments, a practitioner may align the collapsible sheet, such that cells that the practitioner intends to deflate are aligned above the wound at the tissue 350. In some embodiments, the practitioner may selectively deflate one or more cells above the wound tissue. For example, the practitioner may deflate one, two, three, four, or more cells depending on the size and the shape of the wound relative to the size of cells. In some embodiments, the practitioner may deflate wound tissue after negative pressure is provided beneath and/or around the collapsible sheet. In some embodiment, the practitioner may apply negative pressure before negative pressure is provided to the wound. In some embodiments where the collapsible sheet is the outermost layer of the wound closure device, the practitioner may further deflate cells to accommodate to change to the wound during the course of the negative pressure without removing the wound closure device from the patient.

Collapsing of Collapsible Sheet

Figure 5:
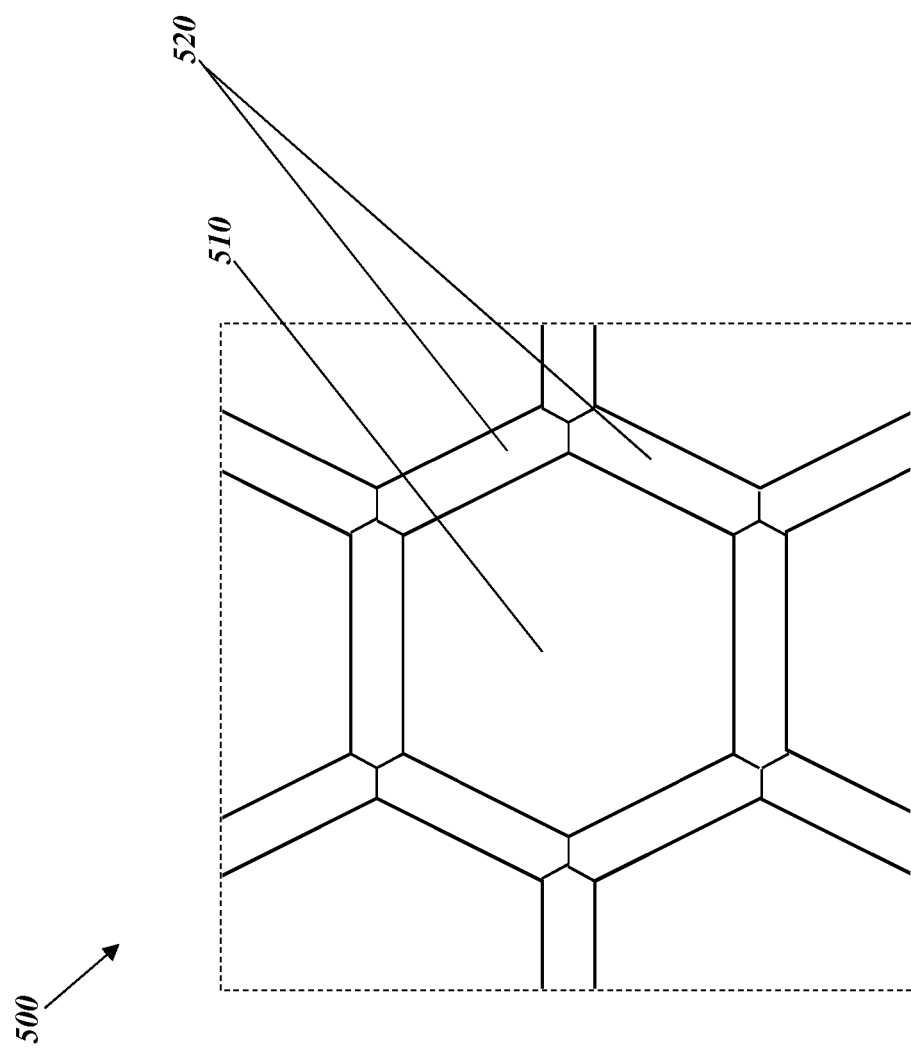
FIG. 5 illustrates a partial top view of an embodiment of a collapsible sheet.

FIG. 5 illustrates an embodiment of a collapsible sheet 500 similar to the collapsible sheets in FIGS. 2-4. Here, the collapsible sheet 500 includes cells 510 provided side-by-side and surrounded by inflatable cell wall sections 520. In some embodiments, at least some of cells 510 are inflatable. In some embodiments, none of the cells 510 are inflatable. A single cell may be surrounded by plurality of inflatable cell wall sections, such as in FIG. 5, where the cell 510 is surrounded by six separated inflatable cell wall sections 520.

In some embodiments, similarly with inflatable cells described in this section or elsewhere in the specification, any one of inflatable cell wall sections 520 may collapse. For example, inflatable cell wall sections 520 may collapse by being punctured, or being opened by removing detachable tabs such as tabs described in relation with FIG. 4. When the collapsible sheet 500 is exposed to negative pressure environment, inflatable cell wall sections 520 may be further collapsed. When one or more inflatable cell wall sections 520 collapses, the cell 510 may be laterally pulled toward the direction of the collapsed cell wall sections 520.

Additionally, collapsed inflatable cell wall sections may be less rigid than other inflatable cell wall sections which are not deflated. When cell(s) collapse, cell(s) may collapse more from being surrounded by more flexible cell walls than by more rigid cell walls. Accordingly, in some embodiments, cells 510 of the collapsible sheet 500 may collapse more from deflated cell wall sections than from inflated cell wall sections. In some embodiments, the practitioner or user of the collapsible sheet 500 may control the direction of collapse of each cells 510 and the collapsible sheet 500 overall, by selectively puncturing or opening the detachable tabs of inflatable cell wall sections 520. For example, the practitioner may deflate one, two, three, or more of the inflatable cell wall sections around a cell before or after the practitioner let the cell collapse. In some embodiments, such direction of collapse may be indicated in each inflatable cell wall sections, for example, by printing directional arrows on cell or tabs, color coding or numbering each inflatable cell wall, or any other mechanisms described elsewhere in the specification or suitable to help the practitioner to selectively deflating inflatable cell walls.

In some embodiments, the practitioner may deflate the inflatable cell wall sections 520 before deflating cells 510. In some embodiments, the practitioner may deflate the inflatable cell wall sections after deflating cells 510 as described in this section or elsewhere in the specification, for example, to further adjust direction and amount of collapse.

Collapsible Sheet with a Port

Figure 6A:
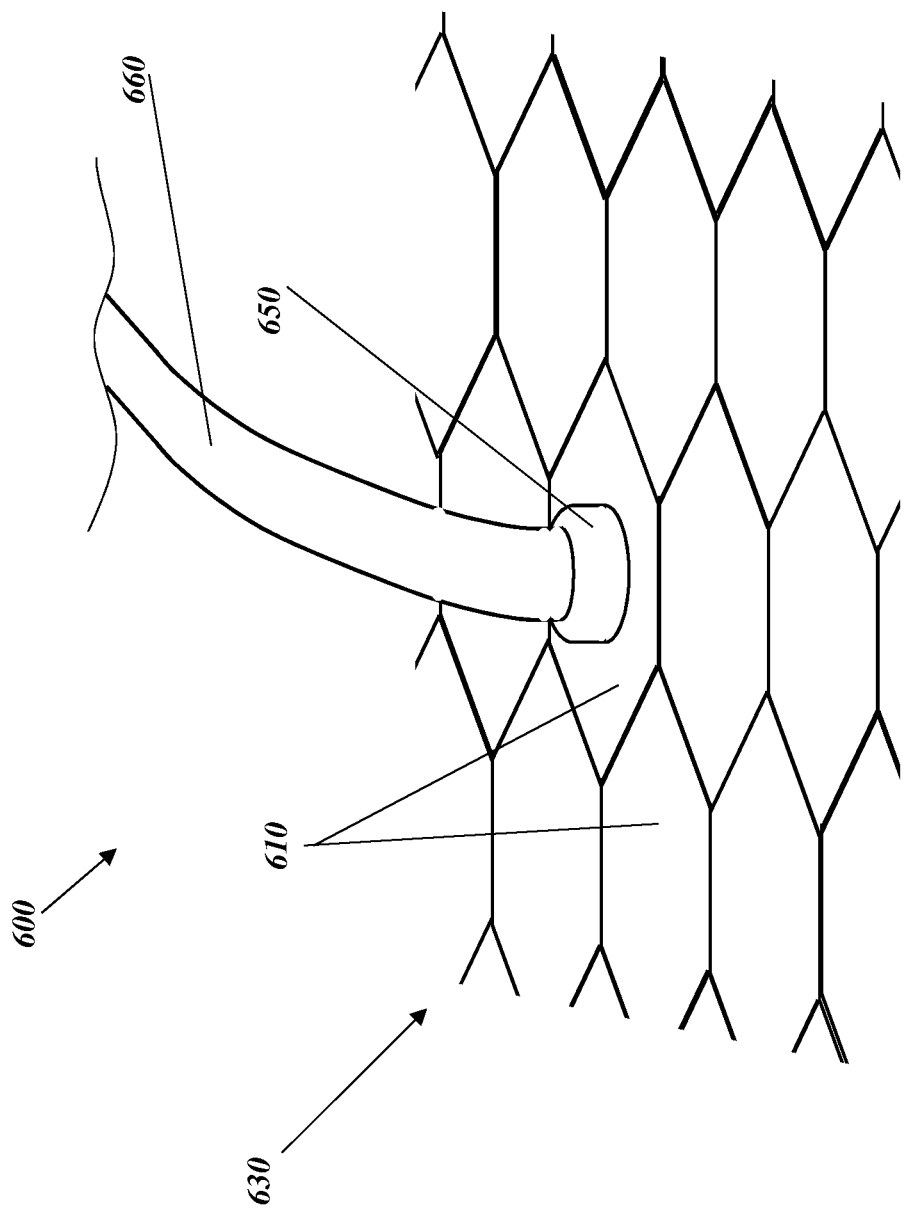
FIGS. 6A-B illustrate embodiments of a collapsible sheet with a port.

FIG. 6A illustrates an embodiment of a wound closure device 600 including a collapsible sheet 630 similar to the collapsible sheets described in relation with FIGS. 2-5 or elsewhere in the specification. Here, the collapsible sheet 630 includes cells 610, and one or more cells have a port 650 which is connected to a source of negative pressure (not shown) via a conduit 660. In some embodiments, the port 650 is configured to deliver negative pressure beneath the collapsible sheet 630. The port 650 may be located at or near the center of the cell 610, or the center of the collapsible sheet 630, such that the port does not easily get sealed off before the collapsible sheet 630 completely collapses.

Figure 6B:
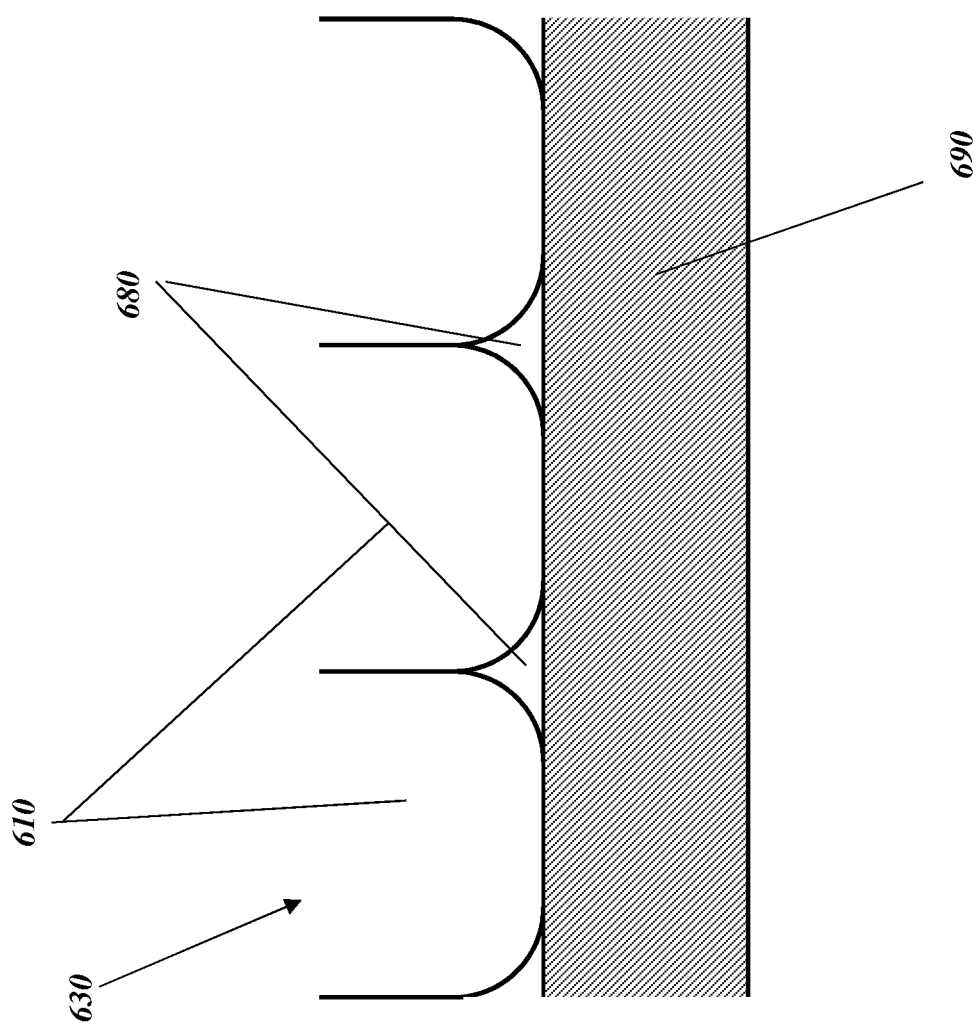

FIG. 6B illustrates the collapsible sheet 630 having cells 610 positioned in and/or over a wound 690. In some embodiments, the collapsible sheet 630 may have gaps 680 between cells 610 and the wound 690, such that negative pressure provided by the port 650 beneath the collapsible sheet 630 can more efficiently propagate across the area where the negative pressure is applied, such as across at least part of the wound 690.

Certain wounds, such as fasciotomy wounds, often exude a lot of wound fluid. In such case, applying negative pressure beneath the collapsible sheet over certain wound area may exert too much stress on the wound from the collapse of the collapsible structure. A port similar with the port 650 of FIG. 6A may include a mechanism to effectively manage negative pressure depending on the status of the wound.

Figure 7A:
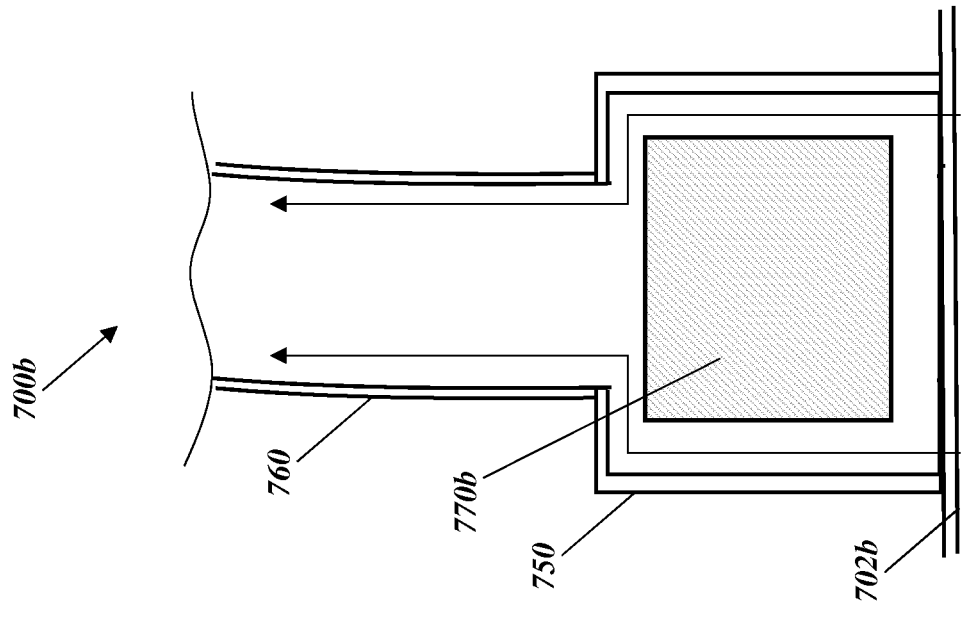
FIGS. 7A-B illustrate embodiments of a valve of a negative pressure treatment system.
Figure 7B:
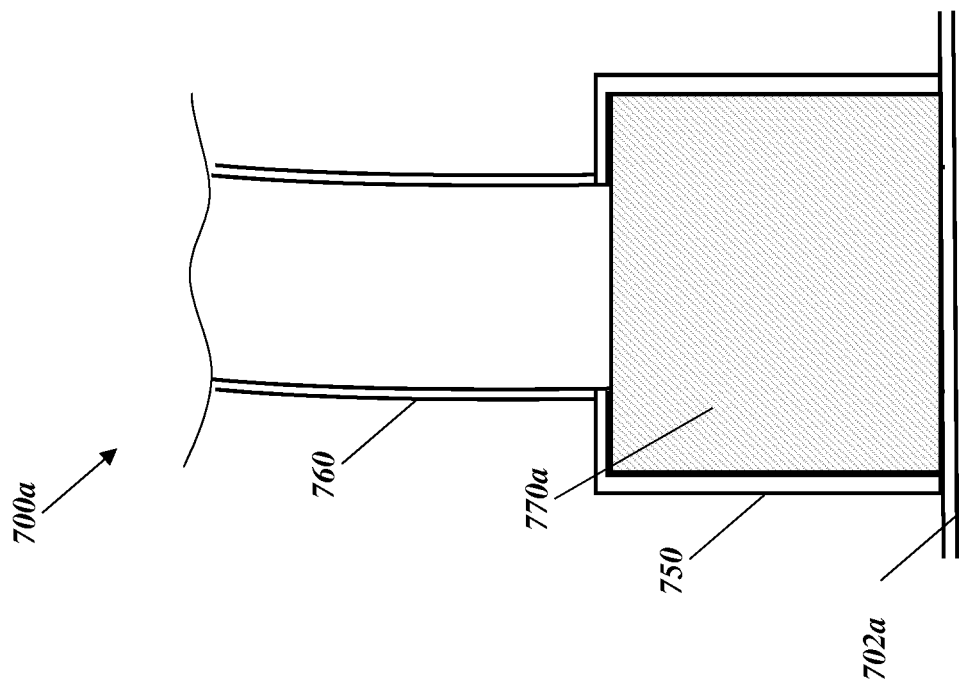

FIGS. 7A and 7B illustrate a schematic view of such an embodiment of a port for negative pressure wound therapy. FIG. 7A illustrates an embodiment of a port system 700a where a wound tissue 702a exudes much fluid, while FIG. 7B illustrates an embodiment of a port system 700b where a wound tissue 702b exudes zero to less fluid.

Port systems 700a and 700b include a valve 750 and a conduit 760 configured to supply negative pressure. The port system 700a of FIG. 7A includes a superabsorber pathway 770a. The superabsorber 770a may be constructed from a superabsorbing material which swells when it has absorbed fluid and contracts when it is dry. Therefore, the superabsorber 770a may swell if rate of absorption of the wound fluid is greater than evaporation of the wound fluid. When the superabsorber 770a has swollen, it may at least partially block the pathway and cause at least some negative pressure from the conduit 750 to not propagate to the wound. However, as the amount of wound fluid is reduced and the rate of evaporation of the wound fluid becomes greater than absorption, the superabsorbing material may contract to its original size as shown by the superabsorber 770b in FIG. 7B. As shown in FIG. 7B, as the superabsorber 770b contracts, it opens the valve and may allow negative pressure to propagate to the wound, allowing additional lateral compression from the collapsible sheet. Therefore the valve 750 may increase the compression from the collapsible sheet as the wound is healing. In some embodiments, the valve 750 may be located at the port, at the conduit, or at the collapsible sheet.

Other Variations

Although this disclosure describes certain embodiments, it will be understood by those skilled in the art that many aspects of the methods and devices shown and described in the present disclosure may be differently combined and/or modified to form still further embodiments or acceptable examples. All such modifications and variations are intended to be included herein within the scope of this disclosure. Indeed, a wide variety of designs and approaches are possible and are within the scope of this disclosure. No feature, structure, or step disclosed herein is essential or indispensable. Moreover, while illustrative embodiments have been described herein, the scope of any and all embodiments having equivalent elements, modifications, omissions, combinations (e.g., of aspects across various embodiments), substitutions, adaptations and/or alterations as would be appreciated by those in the art based on the present disclosure. While certain embodiments have been described, these embodiments have been presented by way of example only, and are not intended to limit the scope of protection.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations.

Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A wound closure device comprising a collapsible sheet configured to be placed over a wound, the collapsible sheet comprising:
a top layer and a bottom layer; and
a plurality of cells at least partially defined by the top layer and the bottom layer, the plurality of cells arranged side-by-side in a horizontal plane and adjoined to one another by a plurality of cell walls;
wherein:
each cell comprises a tessellating shape;
each cell comprises a hollow space enclosed by cell walls, a portion of the top layer, and a portion of the bottom layer, the hollow space configured to be filled with fluid; and
at least one of the plurality of cells has an interior space that is fluidically isolated from all other cells of the plurality of cells and is configured to selectively collapse in a vertical plane of the collapsible structure that is perpendicular to the horizontal plane and thereby cause at least a portion of the collapsible sheet to collapse.

2. The device of claim 1, wherein at least some of the cells are inflatable.

3. The device of claim 1, wherein at least one of the top layer or the bottom layer comprises flexible thin film material.

4. The device of claim 1, wherein at least some of the cells are configured to collapse when negative pressure is applied to the collapsible sheet.

5. The device of claim 1, wherein the plurality of cells have uniform size and shape.

6. The device of claim 1, wherein at least some of the plurality of cells have non-uniform size and/or shape.

7. The device of claim 1, wherein at least some of the plurality of cell walls are inflatable.

8. The device of claim 1, wherein the collapsible sheet further comprises an indicator on one or more cells configured to indicate a direction where the collapsible sheet will collapse upon collapse of any particular cell.

9. The device of claim 1, wherein the collapsible sheet is configured to cover the wound and form a seal around the wound.

10. The device of claim 1, further comprising a suction port configured to supply negative pressure to the wound.

11. The device of claim 10, wherein the port is integrated in the collapsible sheet.

12. The device of claim 10, wherein the port comprises a valve including superabsorbent material configured to swell and at least partially close the valve when a rate of absorption of wound fluid is greater than a rate of evaporation of wound fluid.

13. The device of claim 1, wherein the bottom surface of the collapsible sheet comprises one or more gaps between cells.

14. The device of claim 1, further comprising a tissue protection layer configured to be positioned over the wound below the collapsible sheet.

15. The device of claim 1, further comprising one or more drapes configured to cover the collapsible sheet and form a seal around the wound.

16. A method of treating a wound, comprising:
placing the collapsible sheet of claim 1 over the wound.

17. The method of claim 16, further comprising:
applying or causing application of negative pressure through the collapsible sheet to the wound,
wherein the application of negative pressure causes the collapsible sheet to collapse.

18. The method of claim 16, further comprising placing a tissue protection layer over the wound before placing the collapsible sheet.

19. The method of claim 16, further comprising adhering or sealing the collapsible sheet to an area adjacent the wound.

20. A wound closure device comprising a collapsible sheet configured to be placed over a wound, the collapsible sheet comprising:
a top layer and a bottom layer;
a plurality of cells at least partially defined by the top layer and the bottom layer, the plurality of cells arranged in a horizontal plane; and
a plurality of cell walls;
wherein:
each cell comprises a hollow space enclosed by cell walls, a portion of the top layer, and a portion of the bottom layer, the hollow space configured to be filled with fluid; and
at least one of the plurality of cells is configured to be individually selectively collapsible in a vertical plane of the collapsible structure that is perpendicular to the horizontal plane without other cells of the plurality of cells collapsing in the vertical plane by releasing the fluid that has filled the hollow space in each cell through an opening in the top layer, thereby causing at least a portion of the collapsible sheet to collapse when the at least one of the plurality of cells is collapsed.

* * * * *